(12) United States Patent
Martino et al.

(10) Patent No.: US 6,867,861 B2
(45) Date of Patent: Mar. 15, 2005

(54) METHOD AND APPARATUS FOR CHARACTERIZING THE COLOR PROPERTIES OF FLUIDS

(75) Inventors: Anthony Joseph Martino, West Chester, PA (US); Ken Stephen Schermacher, Chadds Ford, PA (US); Kelly Regan Smolcynski, Media, PA (US); Michael P. Milone, Pittsgrove, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/097,416

(22) Filed: Mar. 13, 2002

(65) Prior Publication Data

US 2002/0167663 A1 Nov. 14, 2002

Related U.S. Application Data

(60) Provisional application No. 60/276,968, filed on Mar. 19, 2001.

(51) Int. Cl.[7] ............................. G01J 3/42; G01J 3/50
(52) U.S. Cl. ...................... 356/319; 356/410; 356/413; 356/246
(58) Field of Search ................ 356/319, 323, 356/325, 410, 413, 440, 246

(56) References Cited

U.S. PATENT DOCUMENTS

| | | | | |
|---|---|---|---|---|
| 3,740,156 A | * | 6/1973 | Heigl et al. ................. | 356/246 |
| 4,403,866 A | | 9/1983 | Falcoff et al. | |
| 4,511,251 A | | 4/1985 | Falcoff et al. | |
| 4,786,171 A | * | 11/1988 | LeFebre et al. ............. | 356/326 |
| 4,872,753 A | * | 10/1989 | Danigel et al. ............. | 356/246 |
| 4,887,217 A | | 12/1989 | Sherman et al. | |
| 4,890,920 A | | 1/1990 | Niziolek et al. | |
| 4,936,685 A | | 6/1990 | Taylor et al. | |
| 5,078,493 A | | 1/1992 | Evens et al. | |
| 5,268,736 A | * | 12/1993 | Prather ....................... | 356/246 |
| 5,442,437 A | * | 8/1995 | Davidson .................... | 356/246 |
| 6,056,790 A | * | 5/2000 | Clark et al. .................... | 8/502 |
| 6,515,748 B2 | * | 2/2003 | Walker et al. .............. | 356/246 |
| 6,536,649 B1 | * | 3/2003 | Master et al. .............. | 228/49.5 |

FOREIGN PATENT DOCUMENTS

| | | |
|---|---|---|
| BR | PI9800361-5 | 2/1998 |
| DE | 25 25 701 A1 | 12/1976 |
| DE | 240 075 A1 | 10/1986 |
| FR | 2 594 131 A1 | 8/1987 |
| GB | 1 589 705 | 5/1981 |
| SU | 364877 | 11/1973 |
| WO | WO 99/48602 A1 | 9/1999 |

OTHER PUBLICATIONS

Anonymous, Colour measuring of wet coating compositions, Research Disclosure—Nov. 1991. RD 33196.

* cited by examiner

*Primary Examiner*—F. L. Evans
(74) *Attorney, Agent, or Firm*—Steven C. Benjamin

(57) ABSTRACT

An apparatus for inspection of fluids, particularly dispersions and tints, having a fluid analysis cell with a cavity therein defining a fluid analysis chamber, fluid inlet and outlets extending from the cavity in opposite directions to enable fluid flow into and out of the analysis chamber, and a light transmitting probe and a light receiving probe extending within the cavity juxtaposed from each other across the flow path in spaced apart relation, with the probes being movable relative to each other, thus providing a fluid analysis chamber having an adjustable pathlength and allowing flow across and around the faces of the probes for pressure relief of the fluid, to provide accurate color measurements. The apparatus is particularly useful in the manufacture of dispersions and tints used in the manufacture of paints, so that the color of material being made can be accurately matched to a standard color in the wet state with confidence that the color will match in the dry state.

10 Claims, 4 Drawing Sheets

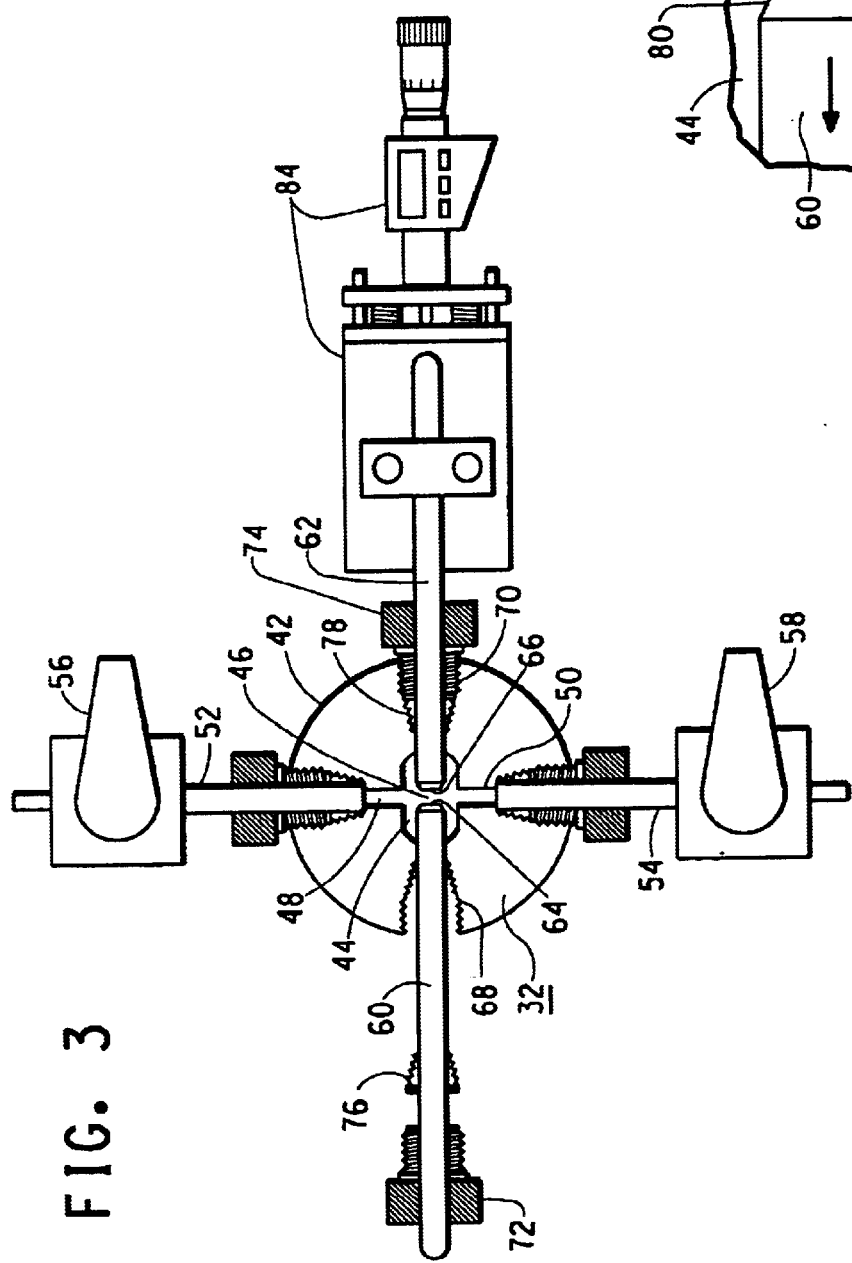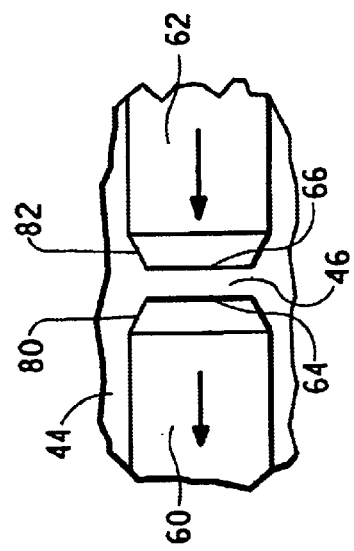

METHOD AND APPARATUS FOR CHARACTERIZING THE COLOR PROPERTIES OF FLUIDS

CROSS-REFERENCE TO RELATED APPLICATION

This application claims priority under 35 U.S.C. §119 from U.S. Provisional Application Ser. No. 60/276,968 (filed Mar. 19, 2001), which is incorporated by reference herein for all purposes as if fully set forth.

BACKGROUND OF THE INVENTION

This invention relates to a method of and apparatus for the inspection of fluids. In particular, the invention relates to an improved apparatus for measuring the color properties of fluids, in transmission, such as pigment dispersions and tints, flowing through the apparatus.

Pigment dispersions and tints are widely used nowadays in formulating high performance coating compositions used in particular for exterior finishes for automobiles and trucks.

In the manufacture of such dispersions and tints, one problem is to measure the color and strength of the material as it is being made, so that adjustments can be quickly made to bring this material within acceptable color tolerance values. Color measurements nowadays are carried out by a manual process, which involves taking an aliquot of the material, blending it with a standard white or black paint, spraying out the blends as a coating onto panels, baking and drying the panels, and then measuring one or more color properties of the dried coating using a colorimeter or spectrophotometer against a standard. Adjustments are then made to the batch until the color parameters match those of the standard.

Color measurement by this method is very time consuming because of sample preparation and drying times. Also, this procedure may have to be repeated numerous times before the desired color property is achieved. Another problem which arises with this procedure is that the accuracy of the test is dependent on the color and strength stability of the standard white or black paints. Even with careful control, these standards tend to vary from batch to batch and also tend to flocculate or settle in time, leading to poor test repeatability and making it very difficult to accurately analyze the color and strength of the batch as it is being made.

The aim within the industry for some time has been to measure the color properties of these fluids in a wet state and in a way which predicts the color of the fluid when applied and dried. The primary benefits are mainly associated with time savings although some are associated with the increased likelihood of an automated manufacturing process.

Conventional laboratory spectrophotometers, employing cuvette-type sample chambers, have been proposed to make such wet measurements off-line by measuring a transmission spectrum of a wet transparent sample. However, cell pathlengths in such spectrophotometers are, in general, too large for such measurements. Moreover, settling and flocculation can also occur, changing the color of the sample.

Another instrument, described in Batista et al. WO 98/16822, published Apr. 23, 1998, employing a variable pathlength fluid measurement cell to measure properties of fluids, including color, could be used for such measurements. However, this equipment possesses multiple moving parts which are part of the fluid path, which can cause difficulty in cleaning, and are difficult to maintain. Another disadvantage is that the design is such that it requires high volumes of fluid sample to take proper readings.

Therefore, there is still a need to provide a method and apparatus for color measurement of wet fluids that: produces acceptably consistent results; does not require the spraying and blending with white or black standards and the production of a number of dry samples; cleans rapidly (within 1 or 2 minutes) so that the cycle time of the measurement is extremely small compared to process changes; provides an easy means (including automatic) of delivering samples to the analysis cell so that fluid measurements of color and strength can be made rapidly; and predicts with confidence that the wet readings will also match the standard in the dry.

In addition to the above features, there is also a need to provide a method and apparatus that can be made intrinsically safe, so that it can be placed on a plant floor in an environment wherein may be contained an explosive atmosphere.

There is yet a further need to fully characterize the color and strength properties of these kinds of fluids off-line (e.g. in a control laboratory or color development facility), thus providing a more versatile instrument.

SUMMARY OF THE INVENTION

An apparatus for inspection of fluids having the following components:

a fluid analysis cell having a cavity therein for measuring light transmittance of a sample;

a fluid inlet and outlet channel extending from the cavity in opposite directions to enable fluid to flow into and out of the fluid chamber;

an optional pressure vessel, in which a fluid sample is placed, and which, by means of pressurization, delivers the sample to the fluid analysis cell;

a light transmitting probe and a light receiving probe positioned within said cavity, the probes being juxtaposed from each other across the flow path in spaced apart relation, wherein the probes extend within the cavity a distance to allow the fluid to flow across the faces of the probes as well as around the faces to provide for pressure relief of the fluid being tested, and further wherein the probes are movable relative to one another to allow for adjustment of the space therebetween which forms the optical viewpath; and a light source and a spectrophotometer, preferably a flash lamp and a dual beam spectrophotometer, associated with and connected to the probes preferably via single-fiber fiber optic cables for directing light to the fluid analysis cell and detecting light therefrom respectively to measure color parameters of the fluid passing through the cell by transmittance.

A method for measuring the color properties of a fluid using the above apparatus is also a part of this invention.

Preferably the apparatus as designed possesses a manually operated sample system and a non-purged enclosure for operation in a general laboratory.

In an alternative embodiment, the apparatus also contains:

a purged explosion-proof enclosure for containing all electrical/electronic components, as well as the light source for the instrument, so that the instrument may be operated in an environment possibly containing explosive atmospheres, such as a manufacturing plant floor for at-line measurements; and an automatic pneumatically-controlled sample system for delivery of the sample to the fluid analysis chamber.

BRIEF DESCRIPTION OF THE DRAWINGS

FIG. 3 is a front, partial cutaway, view of the flow-through fluid analysis cell used in the apparatus of FIG. 1.

FIG. 4 is a cross-sectional view showing the central cavity of the fluid analysis cell of FIG. 3.

DETAILED DESCRIPTION OF THE PREFERRED EMBODIMENTS

The present invention provides a method and apparatus to filly characterize the color and strength properties of fluids such as tints, paints, dispersions, and inks off-line in the wet state. This has not heretofore been possible with conventional equipment.

Because the above fluids are complex suspensions of pigment particles and/or other scattering agents, the color (hue, chroma, lightness) of said fluids in the wet state is not necessarily the same as in the dry state. Thus, it is simply not sufficient to measure colors in the wet state alone without providing a connection to the dry color measurements, because it is well known that when fluids such as paints, tints, dispersions, or inks dry, their hue, chroma, and lightness can change either collectively or individually. Therefore, in order to adequately predict color modifications in the dry state from measurements made in the wet and fully characterize these fluids, it is necessary to construct a pathway to map such modifications from wet to dry. The apparatus herein described enables that to be accomplished.

To fully characterize the color and strength properties of said fluids, it is necessary to dilute the fluids and/or view their transmitted light spectra at various optical pathlengths, especially since those color and strength properties vary with the concentration and/or particle size of the suspended particles in the fluid. This variation has a significant impact on the alteration of color properties, or shading, of said fluids. Therefore, one needs to perform that shading at a specific state of transparency (or lightness, depending on the hue of the colorants) in the wet state that corresponds to the dry state when the fluid is blended with white or black for reflectance measurements. This is to assure that said color alteration in the wet state will alter the color metrics (such as L*, a*, b*, c, h and etc.) in the same way as in the dry.

To overcome the foregoing inherent fluid complexity issues and shading difficulties, the apparatus of the present invention provides the capability to alter the optical pathlength of the fluid analysis cell continuously, and with very little operator effort, over a measurement range in which the fluid in the measurement cell is at least somewhat transparent.

Figure 1:
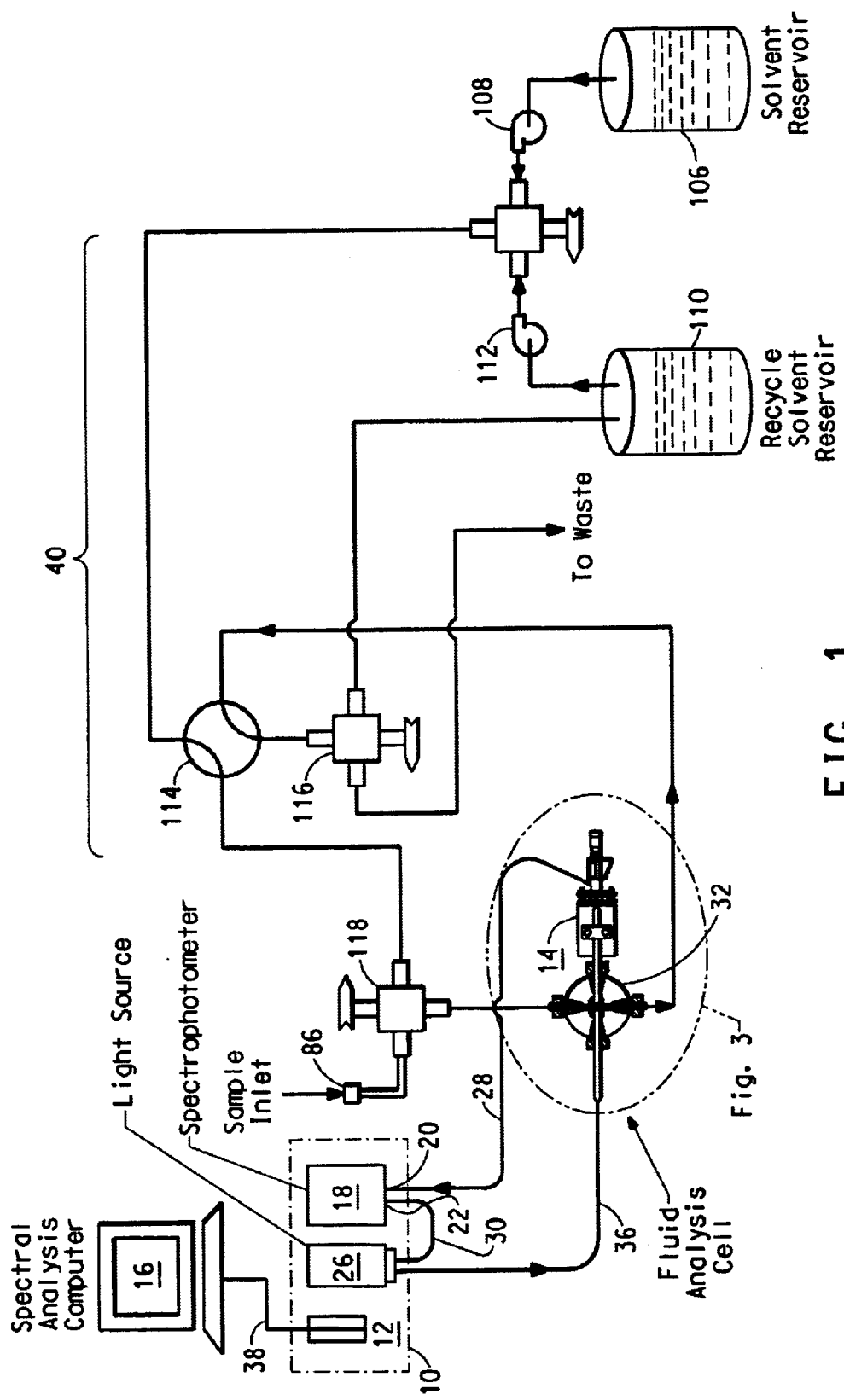
FIG. 1 is a schematic view of the apparatus in accordance with the invention, showing all flow connections.
Figure 2:
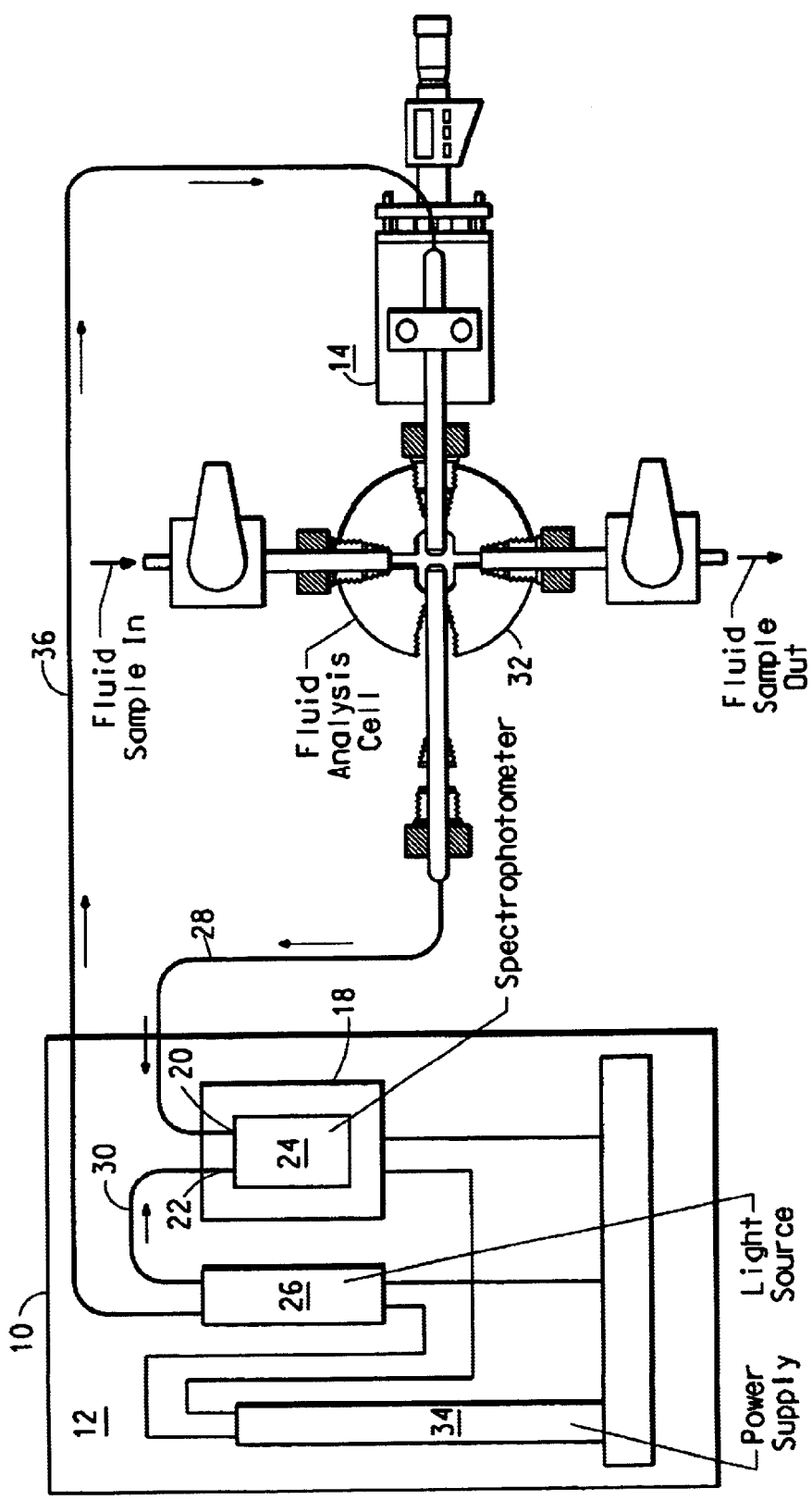
FIG. 2 is a partial view of the apparatus of FIG. 1, showing only the optical unit and flow-through fluid analysis cell sections of the apparatus.

Referring now to FIGS. 1 and 2 of the drawings, the apparatus according to the invention comprises a housing 10 which contains an optical unit 12, for providing a source of visible light to a fluid analysis unit 14 and for detecting the visible light emitted therefrom. Both the optical unit 12 and fluid analysis unit 14 are connected to a system control unit, preferably a computer, 16 for data acquisition, spectral analysis, and control of the functions of units 12 and 14.

The optical unit 12 preferably comprises a dual beam spectrophotometer 18 having two inputs 20 and 22 for detecting light over the visible spectrum from 400 nm to 700 nanometers (nm), preferably in 10 nm increments, a diffraction grating (not shown) for dispersion of the light signals, and a photodiode array detector 24 (incorporated therein). One input 20 collects light from the fluid sample under analysis, while the other 22 collects light directly from light source 26, and provides a reference signal, so that corrections may be effected for variations in the light source intensity. Light is provided to the inputs 20 and 22, via single-fiber fiber optic cables 28 and 30 interfaced with the sample cell 32 and the light source 26. Preferably, the light source itself contains a shroud (not shown) with a movable shutter (not shown). The light source 26 preferably comprises a halogen flash lamp, e.g., a xenon flash lamp, that emits light over a range of wavelengths from 400 to 700 nanometers (nm). The lamp is powered by a standard AC/DC power supply 34 and is monitored with respect to its performance so that it may be changed as soon as it goes below specification.

The shutter (not shown) is used to block the light emitted from the flash lamp during the calibration step, so that a dark current measurement may be made. Also, a set of optical filters (not shown) contained within the flash lamp shroud (not shown) are preferably used to vary the intensity of light emitted from the flash lamp, which: 1) enables the optical unit to make color measurements in its optimum condition, without saturation by high intensity light, or lack of resolution with low intensity light; and 2) ensures that optical signals to both sides of the dual beam spectrophotometer are balanced photometrically.

As shown in FIG. 2, in order to allow for transmission of light to the sample being tested, the flash lamp 26 is also connected via a single-fiber fiber optic cable 36 to the fluid analysis unit 14, as will be described below. Thus, the transmitted light beam emitted from fiber optic cable 36, after passing through the fluid analysis unit 14, is then directed through the return fiber optic cable 28 to input 20 of the spectrophotometer 18 and thereby to its detector 24 for spectral analysis.

Preferably, when the light from either input 20 or 22 enters the spectrophotometer 18 through its entrance slits (not shown), it first strikes a concave reflecting diffraction grating (not shown), which disperses the light into its characteristic wavelengths and reflects it to a photodiode array detector 24 (not shown in detail). The light from one input then proceeds to one half of the detector array, while the light from the other input proceeds to the other half of the array. The diffraction grating within the spectrophotometer together with the entrance slits thus enables the detector to detect single frequency radiation and defines the wavelength resolution of the spectrophotometer.

The detector 24 is a standard photodiode array which comprises a high sensitivity array of photodiodes connected to a low noise amplifier. The detector signal is fed preferably via an RS-232 serial cable 38 to a computer 16 for spectral analysis and L*, a*, b* color value computation, which constitutes the color measurement.

The color technology used for spectral analysis, calculation of the L*, a*, b* color values of the fluid being tested therefrom, and making color comparisons to a standard is well known and fully described in Falcoff et al. U.S. Pat. No. 4,403,866 issued Sep. 13, 1983, which is hereby incorporated by reference herein.

Referring again to FIG. 2, the fluid analysis unit 14 comprises a fluid control unit 40, as will be later described, which supplies a continuous flow of fluid under investigation or reference fluid to a flow-through fluid analysis cell 32.

Referring now to FIG. 3, the fluid analysis cell 32 is designed to provide a fluid stream of uniform color so that accurate color measurements can be made. The cell 32 comprises a cylindrical vessel 42 having a very small central cavity 44 which forms a fluid analysis chamber 46. The central cavity has a spherical shape which is bored along its upper and lower surfaces and along its orthogonal sidewalls. Extending outward in opposite directions from the bores in the upper and lower surfaces of the fluid analysis chamber 46 are fluid inlet and outlet channels 48 and 50, respectively. The juxtaposed alignment of these channels assures unidirectional flow of a fluid sample through the fluid analysis chamber 46 from the inlet channel to the outlet channel. The fluid inlet and outlet channels are threaded to receive an inlet and outlet pipe 52 and 54, respectively. The inlet and outlet pipes include shut off valves 56 and 58 to allow flow through or static color measurements within the cell.

Two transmission probes, 60 and 62, terminating in windows 64 and 66 that are transparent to visible light, are mounted within the bores in the orthogonal sidewalls and extend towards and face each other within the fluid analysis chamber to allow for direct light transmission measurements of the fluid sample within the cell. Thus flow of the sample under analysis is orthogonal to the light transmission path. The axial alignment of the probes enables direct transmission measurements. To secure the probes 60 and 62 and to maintain proper alignment, there are fitting bores 68 and 70 disposed in each of the opposite sidewalls which are threaded to receive hollow fittings 72 and 74, along with their respective ferrules 76 and 78, which when assembled together secure said probes. The transmission probes typically comprise fiber optic probes terminating in optically flat windows 64 and 66 made of a durable optical material such as sapphire or quartz, and containing light collimation lenses (not shown). The windows 64 and 66 are preferably affixed to the ends of the probes with seals 80 and 82, beveled about the circumference of the windows. Preferably the seal is made of a substance impervious and chemically resistant to the fluids to be measured in the analysis cell. Transmission probe 60 is fixedly mounted within one threaded bore 68, while the other probe 62 is movably mounted within the opposite bore 70. The movable probe is attached to a precision micrometer 84, preferably a digital micrometer which can read to 0.0001 inch. The space between the probes defines the cell pathlength.

In the present invention, the pathlength is adjustable by moving the movable probe 62 in the direction towards or away from the fixed probe 60 by a turn of the micrometer. When the desired pathlength is reached, the hollow fitting 74 on the sample cell which secures the movable probe 62 is then tightened to fix the pathlength. The cell pathlength may be of any size, although for practical reasons (because of absorbance of the samples being measured) a thickness between 1 and 10 mils (0.001 to 0.010 inch) is usually chosen. As can be seen in FIG. 2, the transmission probes are connected to the optical unit 12 through single-fiber fiber optic cables 36 from the flash lamp 26, and 28 to the spectrophotometer 18, respectively, to enable light to pass through probe 60, then through the fluid analysis chamber 46, and back through the second probe 62 to the optical unit for spectral measurement.

The cylindrical housing 42, inlet and outlet pipes 52 and 54, and the walls of the probes 60 and 62, as shown in FIG. 3, which form the transmission cell 32, are preferably made of materials which are non-reactive with the fluid that is being passed through the apparatus. Typically these components are made of brass, hastelloy, aluminum, or stainless steel, while the window faces of the transmission probe are made of borosilicate glass, quartz, or sapphire. The probes and fluid analysis chamber cavity 44 may also be coated with a fluorocarbon polymer to prevent contaminant build-up on the cell.

The transmission cell 42 of the present invention, as described above, can thus be characterized as a minimal-flow-relief cell. As shown in FIGS. 3 and 4, the ends of the probes 60 and 62 with beveled windows 64 and 66 extend within the fluid analysis chamber 46 a sufficient distance to enable fluid flow not only across the probes, but also around the probes. This allows minimal flow relief of more viscous fluids, and prevents forces that have a tendency to push the probes away from one another and undesirably change the pathlength of the cell while the fluid is being measured, which would lead to inaccurate color measurements. The windows 64 and 66 not only interface with the sample, but also, taken with their beveled seals and the fact that they are juxtaposed from each other across the flow path, form the viewing path and the flow relief path in the nearly spherical central cavity 44 of the fitting. A cross-sectional view of the central cavity of the 4-way fitting is shown in FIG. 4.

The cell also ensures flow through at a uniform shear to provide a constant interface that can be measured and at a sufficient velocity to prevent a build-up of residue on the cell window. Additionally the high shear, enabled by the small size of the cell cavity 44 and the minimal flow relief around the probe windows, provides an efficient means of cleaning the cell cavity and probe windows 64 and 66. The chamber is also designed to provide flow through the chamber in a laminar fashion, which prevents settling or flocculation of any pigment suspended in the fluid, and which provides a sample of uniform color in the viewing area to insure uniform color measurements. The small size of the cavity within the minimal-flow-relief cell also guarantees that most of the fluid will cross the optical view path so as to give a true sample of the fluid.

Another feature of the cell used in the present invention is that the pathlength of light through the sample is fixed during measurement but can be set manually by a turn of the micrometer 84. This enables the equipment to measure transparent as well as opaque fluids which contain high amounts of light scattering pigments which are normally encountered in a paint manufacturing processes. The concept of this invention therefore still holds in the presence of light scattering. The cell pathlength could also be controlled automatically.

Pathlength of the light through the sample is set large enough to allow sufficient light throughput to be accurately measured by the instrument detectors, yet small enough to avoid saturation of the detectors. As indicated above, the pathlength is typically set between 1 and 10 mils. However, for some optically dense dispersions, dilution may be necessary to obtain full spectral information.

Temperature of the measurement cell and the liquid within the cell is preferably held to a narrow enough range (e.g., plus or minus 5° C.) such that thermal expansion does not change the effective pathlength and such that the standard and sample readings are comparable. Temperature control in the present invention is preferably provided by a thermoelectric or vortex-type cooler (not shown) disposed next to the cell to insure a constant temperature of fluid passing through the cell. The test sample and liquid standard should also be measured at the same temperature within this range to insure uniformity.

The fluid flow control unit 40 is also shown schematically in FIG. 1. Generally any type of control unit can be provided which pumps fluid at a uniform velocity into the apparatus through the inlet 48 and into the fluid chamber 46 and across the window faces 64 and 66 of the probes 60 and 62 or optional viewing windows (not shown) and out through the outlet 50. Color measurements can then be made through the windows by transmittance as a sample volume of fluid is passing through the cell.

In the embodiment shown, the fluid control unit 40 comprises a manually operated sample system which provides for injection of sample into the cell 32 through a sample injection port 86 and for sample line and cell cleanout. The fluid control unit or sample system itself may contain pneumatically operated valves (instead of manual ones) and other components such as pumps, temperature and pressure sensors, and a purge air supply, which would preferably be controlled by the same computer 16 which controls the optical unit which gathers the spectral measurements.

As shown in FIG. 1, for static readings, sample (i.e. tint, solvent) may be introduced to the injection port 86 with a syringe (not shown). While readings may be taken statically in some instances, in general the sample is preferably introduced to the injection port by means of a pressure pot assembly 88, shown in detail in FIG. 5, the drive air for which is controlled by a separate valve (not shown), allowing for a flowing measurement. The sample outlet 90 of the pressure pot is connected to sample injection port 86 of the cell for delivery of sample to the cell.

Figure 5:
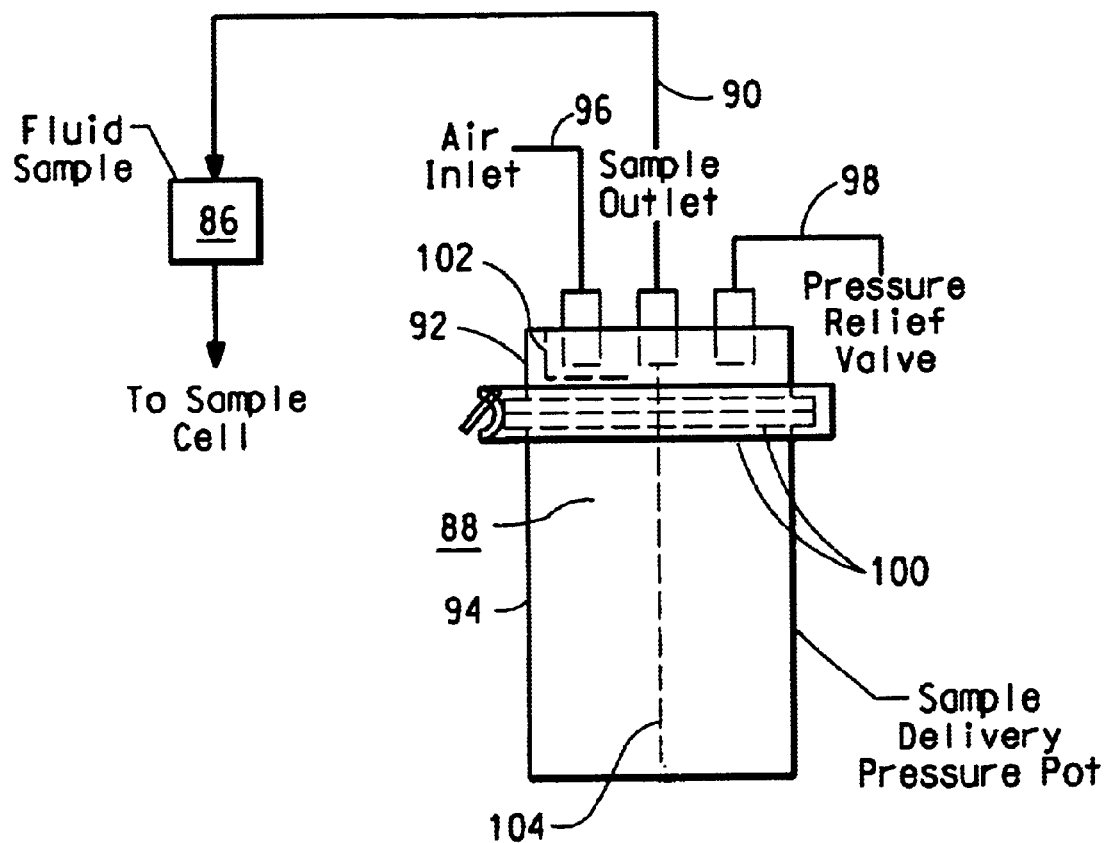
FIG. 5 is a front, partial cutaway, view of the sample pressure pot used in the apparatus of FIG. 1.

The pressure pot assembly 88, shown in FIG. 5, consists of a lid 92, fixedly mounted to a back panel (not shown), as well as a sample pot 94 which contains the sample. The lid contains an air inlet 96 for pressurization of the sample pot, a sample outlet 90 for fluid communication with the sample cell, and a pressure relief valve 98. The sample pot and lid assembly is sealed with a Teflon®-coated neoprene gasket (not shown), which is contained in the sanitary fitting (not shown) between the lid and sample pot. After placing the sample pot with gasket underneath the lid, the two are brought together and sealed by means of a bracket 100, which when tightened, brings both parts of the pressure pot assembly together. The air inlet 96 is shielded from the sample by a baffle 102 to avoid the formation of bubbles or froth in the sample. The sample outlet 90 is connected on the underside to a ¼ inch Teflon® dip tube 104, which extends to the bottom of the pot 94 when it is attached to the lid 92. Thus, as air enters the pot from the top, sample is forced up the dip tube and out of the sample pot, into the cell for a flowing high-shear measurement.

Because the sample flows around the probe faces 64 and 66 within the central cell cavity 44 of the sample cell, as well as being forced through the gap between the faces, cleaning those faces becomes more of an issue than for a zero-bypass flow cell, in that one must attain the necessary shear across the probe windows in order to adequately clean them. Cleanout of the cell may either be accomplished by a simple flush with solvent (or water depending on the carrier solvent), contained in a solvent reservoir 106, by means of a solvent pump 108 connected thereto, or may involve several stages, including flushing with a mixture including a surfactant, contained in a recycle solvent reservoir 110, delivered by means of a recycle solvent pump 112, connected thereto. The latter pumps a mixture of spent cleaning solvent and a surfactant to provide scrubbing action on the windows of the probes thereby removing material deposits. In either case the appropriate shear is developed across the faces of the probes to effect cleaning thereof. As an additional aid to cleaning, flow through the cell 32 may be reversed by means of flow reversal valve 114. Selection of pure solvent versus recycle solvent/surfactant is accomplished by means of valves 116 and 118, operated in tandem. As an alternative, the cleaning solvent may be forced through the sample cell by means of the pressure pot assembly 88, while the "recirculated" solvent can be introduced through the same.

In order to calibrate the cell pathlength, the absorbance of a standard dye of known concentration is measured at several pathlengths to form a calibration curve. Then, by measuring the absorbance maximum of the dye at the given pathlength of interest, one can infer the actual pathlength by use of Beer's Law and the actual absorbance of said dye, and moreover, adjust the pathlength accordingly to the desired value by adjusting the digital reading on the micrometer 84.

To photometrically calibrate the diode array detector 24 of the instrument, the operator manipulates the manual valves, opening a pathway for clean solvent to flow through the analysis cell by means of solvent pump 108. The instrument computer program then records the 100% transmission signal with clean solvent in the cell, to which all subsequent transmission spectra are referred.

To measure a sample of fluid on the instrument, the operator manipulates the manual valves, opening a pathway for sample to flow through the analysis cell 32. Fluid is preferably forced into the cell under pressure, accomplished by means of the sample pressure pot assembly 88.

During the measurement process, light is preferably generated by the xenon flash lamp 26. The dual beam spectrophotometer 18 allows for discrimination of the transmitted light. A reference light path 30 from the flash lamp to the reference channel entrance port 22 of the spectrophotometer is provided for a correction of any lamp intensity fluctuations. A view of the arrangement of the interior of the spectrophotometer cabinet 10 with exterior optical connection to the sample cell is shown in FIG. 2.

The spectrophotometer 18 governs the triggering of the flash lamp 26 and the collecting of data which is then transmitted to a computer via an RS-232 serial link 38. A computer program in turn operates the whole system and collects spectral data from the spectrophotometer. Post-processing of the data in an Excel® worksheet to calculate color metrics, such as L*, a*, and b*, is preferably fully integrated into the program, and results are displayed on-screen as well as stored in Excel® workbooks.

In an alternate embodiment of the apparatus, an automatic, pneumatically controlled sample system is provided to facilitate ease of operation. In addition, an explosion-proof NEMA 4 enclosure containing an appropriate air purge system is provided, so that the instrument may be operated in an environment possibly containing explosive atmospheres, such as a manufacturing plant floor for at-line measurements. However, the system as described above preferably possesses a manually operated sample system and a non-purged enclosure, since the instrument is contemplated for operation in a general laboratory. As it is necessary to calibrate the sample cell pathlength before each measurement, this arrangement is more suitable for development work in a laboratory setting.

The apparatus is specifically designed to measure the color properties of the fluids flowing through the apparatus using wet light transmittance measurements over the visible spectrum in a way that produces accurate instrumental readings. The apparatus can be used in a variety of chemical processes in which color of the resulting product is measured. It is preferably used in a paint, pigment dispersion, ink jet ink, printing ink, or tint manufacturing process. The apparatus of the invention is useful to inspect a wide variety of fluids but is designed particularly to measure the color properties of dispersions and tints that are used in the manufacture of high performance automotive coatings. The apparatus of this invention can be positioned at a remote location from the manufacturing process for either at-line or off-line. The total cycle time of the apparatus as shown in FIG. 1 is a few minutes as opposed to hours using conventional processes. Moreover, it has been found that in making color measurements using this apparatus, there is a good correlation between the color properties of the wet fluid and the corresponding dry coating, which enables visually accurate color matches to be achieved.

What is claimed is:

1. An apparatus for measuring the color properties of a fluid, comprising:

a fluid analysis cell having a cavity therein which forms a fluid analysis chamber for measuring light transmittance of a sample to determine color properties thereof;

a fluid inlet and outlet channel extending from the cavity in opposite directions to enable fluid to flow into and out of the fluid chamber;

a separate fluid delivery system connected to the inlet and outlet channels that draws the fluid sample into and out of the fluid analysis cell;

a light transmitting probe and a light receiving probe positioned within said cavity, the probes being juxtaposed from each other across the flow path in a spaced apart relation, each probe having a face terminating in a viewing window which is transparent to visible light and which projects into the fluid chamber in the path of fluid flow, wherein the probes extend within the cavity to allow the flow across the faces of the probes as well as around the faces to provide minimal flow relief for the fluid, and the probes are movable relative to one another to allow for adjustment of the space therebetween which forms the viewing path, and the viewing windows on each probe are disposed in the path of fluid flow to enable intimate contact with the fluid flowing in the cell.

2. The apparatus of claim 1 in which a light source and a spectrophotometer are associated with and connected to the probes via fiber optic cables for directing light to the fluid analysis cell and detecting light therefrom respectively to measure color parameters of the fluid passing through the fluid analysis cell by transmittance.

3. The apparatus of claim 2 in which the spectrophotometer is a dual beam spectrophotometer and the light source is a flash lamp and the fiber optic cables are single-fiber fiber optic cables.

4. The apparatus of claim 2 in which the probes have beveled faces.

5. The apparatus of claim 2 which further includes:

a pressure vessel, in which a fluid sample is placed, and which, by means of pressurization, delivers the sample to the fluid analysis cell.

6. The apparatus of claim 2 having a fluid analysis cell and a spherical cavity in the center of the cell.

7. The apparatus of claim 2 in which the flow of fluid through the fluid analysis chamber is unidirectional and laminar at a uniform shear.

8. A method of measuring a color property of a wet fluid comprising supplying a sample volume of liquid to a transmission cell, allowing the fluid to pass through the cell and across two viewing probes extending within the cell in intimate contact with the fluid and in juxtaposed, spaced apart relation and moveable relative to one another, directing light from a light source through one of the viewing probes to the fluid analysis cell and detecting light transmitted therefrom through the other viewing probe to measure color parameters of the fluid passing through the cell by light transmittance, and measuring the color property of the sample volume by light transmittance using a spectrophotometer which records the light transmittance through the sample and reports the color properties of the fluid while the sample is in the cell.

9. The method of claim 8 in which the sample is flowing through the cell.

10. The method of claim 9 in which the flow of the sample is unidirectional and laminar.

* * * * *